United States Patent [19]
Janik et al.

[11] Patent Number: 5,404,217
[45] Date of Patent: Apr. 4, 1995

[54] LASER LIQUID FLOW CELL MANIFOLD SYSTEM AND METHOD FOR ASSEMBLY

[76] Inventors: Gary R. Janik, 216 E. Calle Laureles, Santa Barbara, Calif. 93105; John F. Magolske, 122 Natoma Ave., Santa Barbara, Calif. 93101

[21] Appl. No.: 112,105
[22] Filed: Aug. 26, 1993
[51] Int. Cl.6 .......................................... G01N 21/05
[52] U.S. Cl. .................... 356/246; 356/440; 356/410; 250/576
[58] Field of Search .............. 356/246, 410, 411, 440; 250/576

[56] References Cited
U.S. PATENT DOCUMENTS

| | | | |
|---|---|---|---|
| 4,329,048 | 5/1982 | Capitini et al. | 356/410 |
| 4,844,611 | 7/1989 | Imahashi et al. | 356/246 |
| 5,003,174 | 3/1991 | Dätwyler et al. | 356/246 |
| 5,037,199 | 8/1991 | Hlousek | 356/410 |
| 5,120,129 | 6/1992 | Farquharson et al. | 250/576 |
| 5,223,716 | 6/1993 | Rossiter | 356/246 |

*Primary Examiner*—Vincent P. McGraw
*Assistant Examiner*—Jason D. Eisenberg
*Attorney, Agent, or Firm*—Hawes & Fischer

[57] ABSTRACT

The flow cell system and method of the present invention for constructing and operating a light scattering test stand enables close reproducible tolerances to be achieved and automatically ensures the mutual alignment of the structures utilized to maintain stability. Pins and bosses are utilized to maintain alignment of the cell assembly with the read head. The flow cell assembly is held down in the read head independently of the stray light cover. The design of the present invention enables precision alignment reproducibility and ease of use.

27 Claims, 5 Drawing Sheets

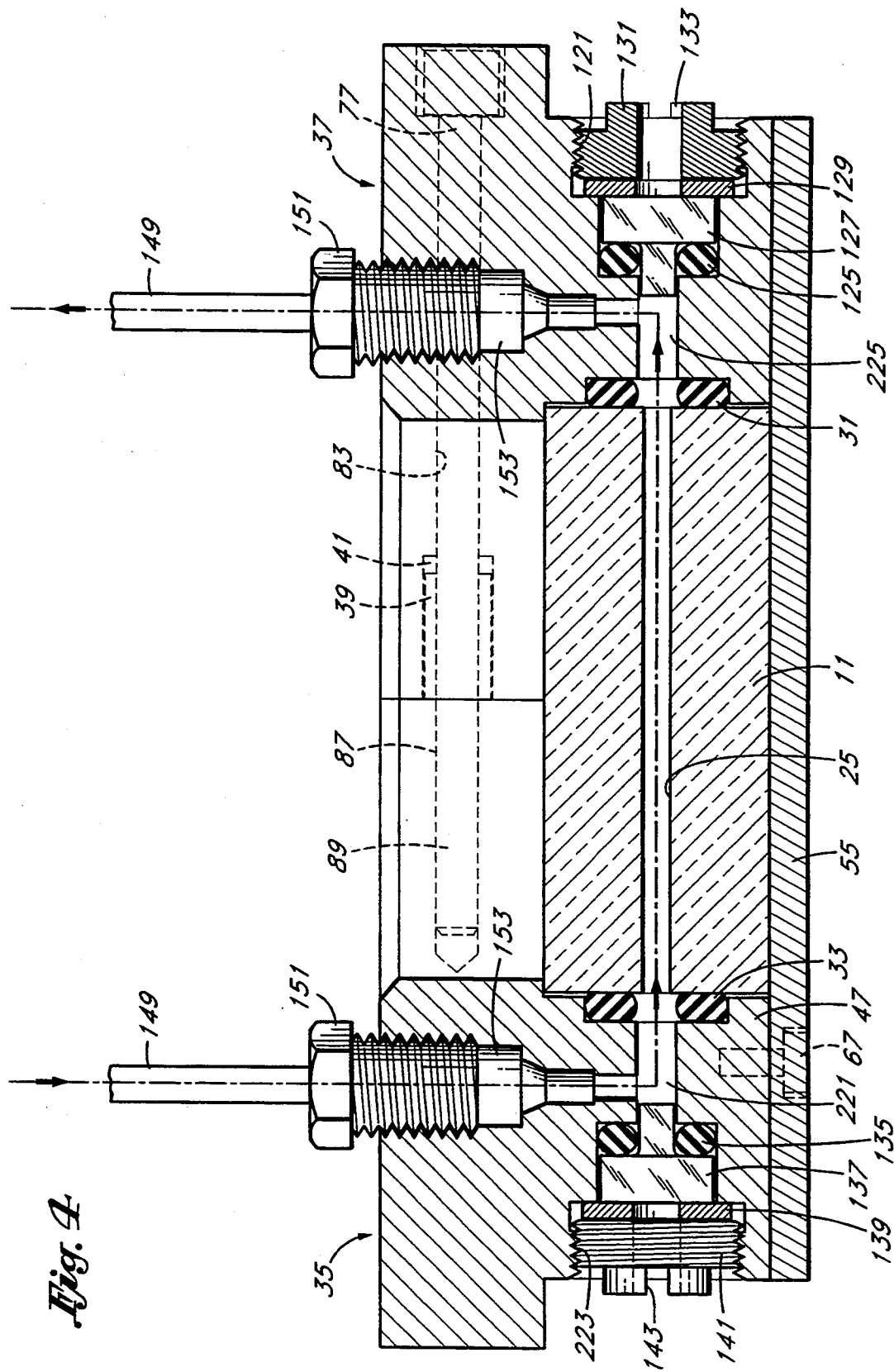

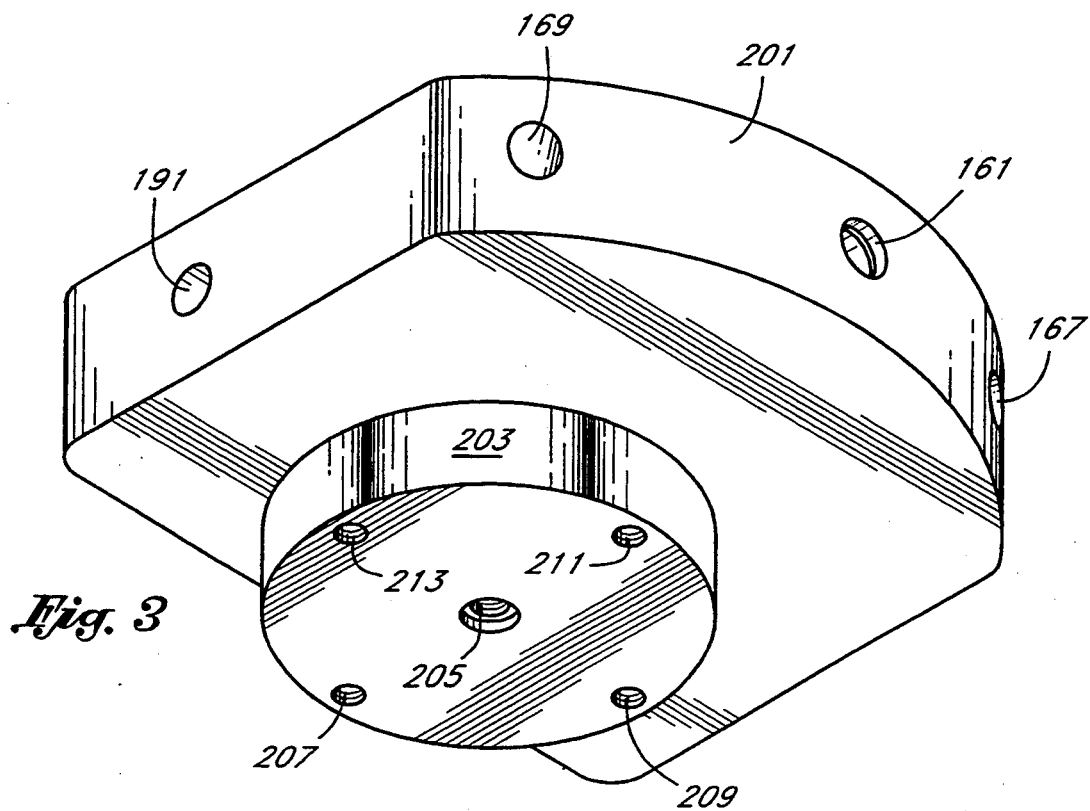
_Fig. 3_
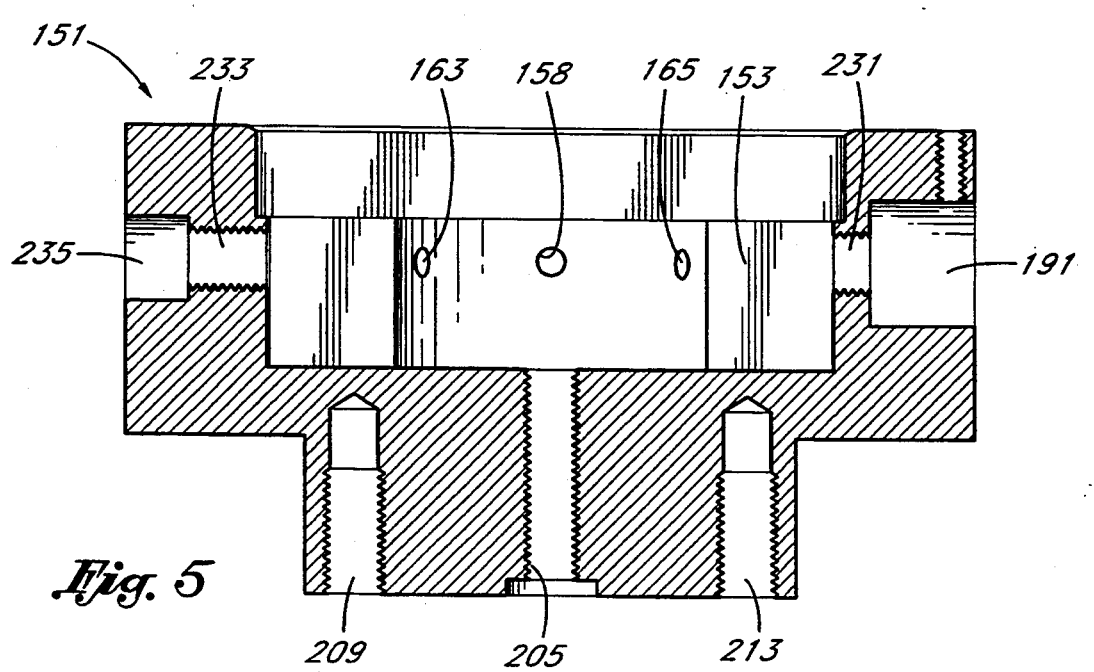
_Fig. 5_

LASER LIQUID FLOW CELL MANIFOLD SYSTEM AND METHOD FOR ASSEMBLY

FIELD OF THE INVENTION

The present invention relates to the field of laser illumination of small particles in liquid media. More specifically, the present invention relates to a device and method for providing high pressure flow of a solvent, and any particles it may contain, coupled with unobstructed laser beam propagation through flow cell bore.

BACKGROUND OF THE INVENTION

Laser flow cells are designed and constructed to enable laser light to more accurately propagate through a liquid media, typically containing dissolved particles. The liquid media presents one or more chemical species to interact with the laser light. The material in the liquid media may be used for light scattering in conjunction with a light scattering read head. The degree of scattering can help to characterize the material carried by the liquid with regard to its molecular weight and the size of its molecules. Typical liquids used are those in which dissolution of the material can be accomplished, and include water and toluene to name but two.

The sample cell configuration includes a flow cell mounted within a support. The flow cell has a bore to carry the fluid, and is surrounded by an array of scattering detectors. The fluid sample is introduced into the bore and is longitudinally illuminated within the bore by a collimated beam of light such as from a HeNe laser or semiconductor laser.

The structures through which the light beam propagates on its way into and out of the bore are matched as nearly as possible to mitigate the effect of any difference in refractive index in the materials. Positional accuracy, precision and reproduciblity is of paramount importance.

Previous flow cells have lacked the accurate and reproducible alignment which is desired in flow cell construction. Aspects of a flow cell tending to degrade its performance include non-alignment of the cell retainers with respect to the cell, of which two are typically used, both with respect to the laser beam and with respect to each other. For example, flow cells which have only seals separating the cell from the cell manifolds will have an alignment dependent upon the skill of the cell assembler.

In some flow cells, the stray light cover was used as an alignment device. The removal of the stray light cover would immediately subject the flow cell to misalignment. In other flow cells, the horizontal alignment depends upon the mating of vertical manifold surfaces with vertical read head surfaces. The tolerances on this fit can not normally be held due to any misalignments occurring in the cell assembly, thus destroying horizontal alignment.

SUMMARY OF THE INVENTION

The flow cell system and method of the present invention encompasses both an apparatus and method enabling close reproducible tolerances to be achieved. The new design of the present invention automatically ensures the mutual alignment of the manifold bores as well as the vertical and horizontal alignment of the cell bore with the manifolds. Pins and/or bosses are utilized to maintain alignment of the cell assembly with the read head. The flow cell assembly is held down in the read head independently of any stray light cover. The design of the present invention enables precision alignment, reproducibility, and ease of use. The techniques outlined in U.S. Pat. No. 4,616,927 issued to Phillips et al, on Oct. 14, 1996 entitled "SAMPLE CELL FOR LIGHT SCATTERING MEASUREMENTS" is incorporated by reference herein.

BRIEF DESCRIPTION OF THE DRAWINGS

The invention, its configuration, construction, and operation will be best further described in the following detailed description, taken in conjunction with the accompanying drawings in which:

FIG. 3 is an underside perspective view of the encapsulation support shown in FIG. 2;

FIG. 4 is a sectional view of the assembled flow cell assembly of FIGS. 1 and 2 taken along line 4—4 of FIG. 2;

FIG. 5 is a sectional view of the encapsulation support shown in FIG. 2 taken along line 5—5 of FIG. 2;

DETAILED DESCRIPTION OF THE PREFERRED EMBODIMENT

Figure 1:
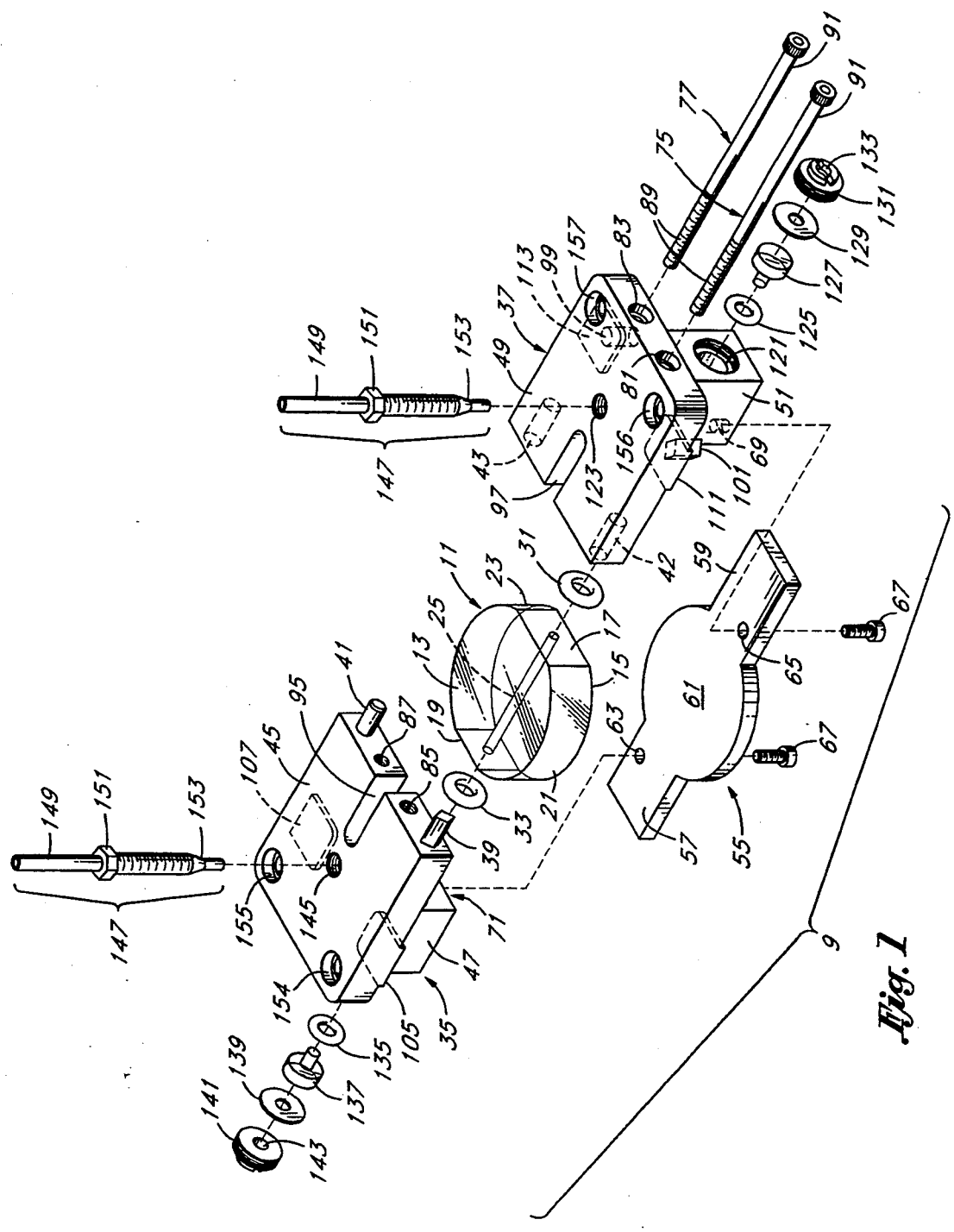
FIG. 1 is an exploded view of the flow cell assembly of the present invention.

The description and operation of the invention will be best described with reference to FIG. 1. FIG. 1 is an exploded view of a flow cell assembly 9 of the present invention. A flow cell 11 is shown which has an upper surface 13, lower surface 15, a first end surface 17, a second end surface 19, a first curved surface 21 and a second curved surface 23. A flow bore 25 extends through the flow cell 11 having a first open end opening into first end surface 17 and a second open end opening into second end surface 19. In the configuration shown, laser light entering the flow bore at one end of the flow cell will impinge upon the flowing fluid as it flows longitudinally through the flow cell 11. The other structures to be shown are for their purpose of supporting the flow cell 11, managing the flow through the flow bore 25, and mitigating the effect of any changes in refractive index experienced by the light beam as it travels through the supporting structure. Sensors are positioned along the first and second curved surfaces 21 and 23.

Adjacent the first and second end surfaces 17 and 19 are a pair of o-rings 31 and 33, respectively. The 0-rings 31 and 33 provide sealing of the flow bore 25 at the ends of the flow cell 11. At the left, a first manifold section 35 is shown opposing a second manifold section 37 located at the right. The first manifold section 35 has a pair of locating pins 39 and 41. Locating pin 39 has a diamond cross sectional area while locating pin 41 has a round cross sectional area.

Locating pins 39 and 41 fit into round apertures in the second manifold section 37 which are numbered 42 for the locating pin 39 and 43 for the locating pin 41. The first manifold section 35 has an upper planar portion 45 and a base portion 47. Similarly, the second manifold section 37 has an upper planar portion 49 and a base portion 51. Base portions 47 and 51 of first and second manifold sections 35 and 37 are designed to fit on a base plate 55. Base plate 55 has a pair of rectangular ends 57 and 59 which are continuous with a circular center section 61.

Rectangular end 57 carries a through aperture 63 while rectangular end 59 carries a through aperture 65. A pair of bolts 67 are designed to fit through the apertures 63 and 65 to engage threaded bores 69 and 71, respectively shown in phantom and located in the underside of the base portions 47 and 51. Aperture 71 is shown by direction along a dashed line extending toward base portion 47. Shown adjacent to second manifold section 37 is a pair of bolts 75 and 77 which will extend through a pair of open bores 81 and 83, both of which have counter bores, and into threaded bores 85 and 87 in the first manifold section 35. Bolts 75 and 77 have a threaded end sections 89 and smooth cylindrical sections 91 to facilitate their axial movement through the open bores 81 and 83.

Note that first manifold section 35 is formed with a slot 95 while second manifold section 37 is formed with a slot 97 opposing slot 95. The slots 95 and 97 enable viewing of the flow cell 11 when the manifolds 35 and 37 are joined. The second manifold section 37 has two vertical pins 99 and 101 embedded in its lower surface, and protruding down. One pin 99 is round while the other pin 101 is diamond shaped. Both manifold sections 35 and 37 each have a pair of downwardly extending flat bosses. Manifold section 35 has flat bosses 105 and 107 while manifold section 37 has flat bosses 111 and 113 protruding from their lower surfaces.

Base portion 51 has an optical aperture 121 which provides optical alignment with flow bore 25 when the flow cell assembly 9 is assembled. Within the second manifold section 37, a flow conduit (not yet shown) is also in fluid communication with a path between optical aperture 121 and flow bore 25. Optical aperture 121 is in fluid communication with a tap 123 atop the second manifold section 37. During operation, the optical aperture 121 will be sealed, with the flow path to flow bore 25 occurring via the tap 123.

Adjacent the optical aperture 121 is an exploded arrangement of structures which will be inserted into optical aperture 121 to both seal it from a fluid standpoint and to permit light to be directed through the optical aperture 121 and flow bore 25. Most closely adjacent the optical aperture 121 is another o-ring 125 seal. Adjacent o-ring seal 125 is an optical window 127. Optical window 127 has an anti-reflective coating on its outer surface and optionally on its inner surface, to minimize the reflectivity due to changes in the index of refraction of the light path.

Adjacent the Optical window 127 is a plastic washer 129 which is utilized to insulate and space the optical window 127 farther into the aperture 121. Adjacent the plastic washer 129 is a threaded window retainer 131. Window retainer 131 has a concentric bore 133 and is threadably securable into optical aperture 121. The force of compression of the optical window 127 against the o-ring seal 125 against a structure to be shown within the second manifold section 37 seals off any fluid from contact with the outwardly disposed surface of the optical window 127, plastic washer 129 and the inside of concentric bore 133. When threaded window retainer 131 is fully engaged, the washer 129 seats against a surface in second manifold section 37 preventing threaded window retainer 131 from engaging any further and providing a fixed amount of compression for o-ring seal 125. This also keeps the outer window surface of optical window 127 in a fixed position, independent of operational adjustment.

Similarly, with regard to the first manifold section, there is an optical aperture (not shown in FIG. 1) as well as an o-ring 135 seal, optical window 137, plastic washer 139, threaded window retainer 141 having a concentric bore 143. First manifold section 35 is also fitted with a tap 145 to complete the fluid path from the flow bore 25 in a manner similar to that for second manifold section 35.

The taps 123 and 145 are designed to interfit with an identical pair of chromatography tubing assemblies 147. Tubing assemblies 147 each include a chromatography tube 149 (a section of which is shown in FIG. 1) extending into a compression nut 151 which acts on a ferrule 153 to form a seal with the taps 123 or 145 when inserted therein and tightened.

Also shown with respect to the flow cell assembly 9 is a pair of apertures 154 and 155 on upper planar portion 45 and a pair apertures 156 and 157 on upper planar portion 49. The apertures 154, 155, 156 and 157 all have counterbores and will be used to anchor the flow cell assembly 9 into an encapsulation support shown in FIG. 2, to form a completed test stand.

Figure 2:
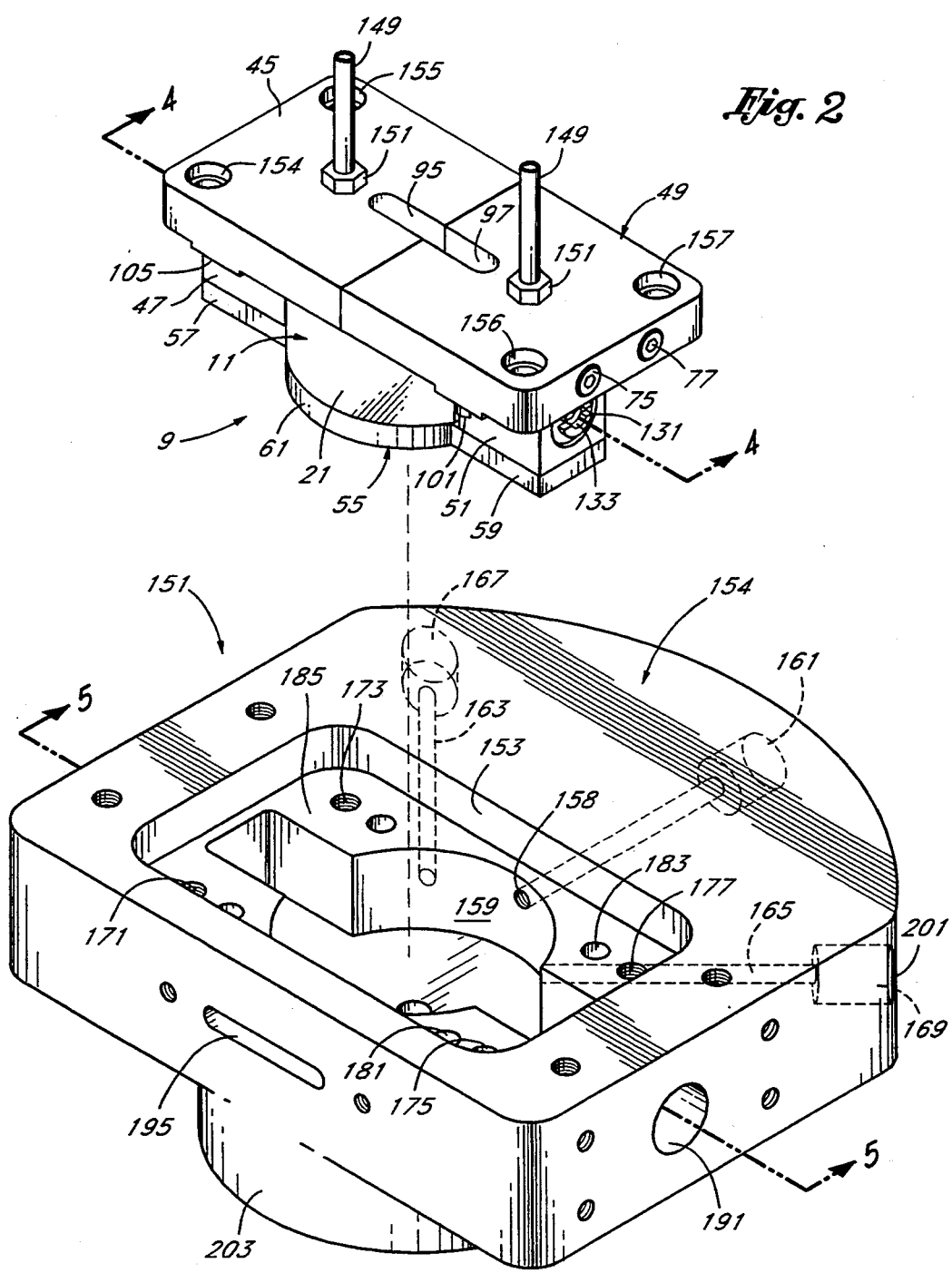
FIG. 2 is an exploded view of an assembled flow cell assembly of FIG. 1 of the present invention with respect to an encapsulation support, which when joined together will form a test stand.

Referring to FIG. 2, a perspective view of the flow cell assembly 9 in assembled form is shown over an encapsulation support 151. A dashed line shows the orientation and fit with which the flow cell assembly 9 is received into an accommodation space 153 in the upper portion of the support 151. Once the flow cell assembly 9 is fitted within the accommodation space 153, the upper planar portions 45 and 49 should fit flush with an upper surface of the encapsulation support 151.

As can be seen with regard to FIG. 2, the accommodation space 153 has several structures which cooperate with structures previously shown on the flow cell assembly 9. Shown in dashed line format, a light transmission bore 158 opens onto a curved wall 159. The bore 158 is at a right angle to the direction of flow which will occur in flow bore 25 when the flow cell assembly is fitted into the encapsulation support 151. Curved wall 159 will lie adjacent the second curved surface 23 of the flow cell 11. Light transmission bore 158 has an enlarged diameter portion 161 at its other end. Another pair of light transmission bores 163 and 165, having enlarged diameter portions 167 and 169, respectively lie at an angle, within the horizontal plane, of 45° from the light transmission bore 158.

A set of four threaded apertures 171, 173, 175 (not visible in FIG. 2) and 177 are arranged to align with apertures 154 and 155 on upper planar portion 45 and a pair of apertures 156 and 157 on upper planar portion 49, respectively. The threaded apertures 171, 173, 175 and 177 will engage bolts (not shown) which hold the flow cell assembly 9 into the encapsulation support 151.

Two vertical holes 181 and 183 extend down from a surface 185 of the accomodation space 153. These vertical holes accept the two pins 101 and 99 protruding from the bottom of the second manifold 37 and align the cell assembly 9 accurately in the horizontal plane. The four bosses 105, 107, 111, and 113 protruding from the bottom of the manifold sections 35 and 37 accurately space and level the cell assembly 9 from the surface 185 of the accomodation space 153 and prevent rocking of the cell assembly 9.

Encapsulation support 151 also includes a first laser port 191 in alignment with concentric bore 133 of threaded window retainer 131. The alignment will occur once the flow cell assembly 9 is lowered into the accommodation space 153 of encapsulation support 151. A second laser port (not shown) is in alignment with concentric bore 143 of threaded window retainer 141. A slot 195 extends into the accommodation space 153 in alignment with the flow cell 11, to provide viewing of the flow cell bore 25.

Encapsulation support 151 has a generally large upper portion 201 supported by a round base 203. Referring to FIG. 3, a view from the underside of the encapsulation support 151 illustrates the round base 203 having been fitted with a central aperture 205, surrounded by four evenly distributed smaller threaded apertures 207, 209, 211, and 213. The central aperture 205 provides a safe path for accidental leaks to be drawn away.

Referring to FIG. 4, a section taken along line 4—4 of FIG. 2 shows the relationship of the internals of the flow cell assembly 9, as it is assembled in FIG. 2. As it can be seen, the liquid flow, as indicated by a dashed line arrow, enters chromatography tube 149, past the compression nut 151 and into a small bore 221 adjacent the optical aperture 223 which was not shown in FIG. 1. The fluid path continues past the o-ring 33, flow bore 25, o-ring 31, and small bore 225 adjacent the optical aperture 121. The flow path turns upwardly, flowing into ferrule 153, past the compression nut 151 and onwardly through the chromatography tube 149.

Laser light will propagate through concentric bore 143 of the threaded window retainer 141, the center of plastic washer 139, optical window 137, o-ring seal 135, through the small bore 221, the center of o-ring 33, flow bore 25, o-ring 31, small bore 225 o-ring 125 seal, optical window 127, the center of plastic washer 129, and concentric bore 133 of threaded window retainer 131. The direction of flow, of course, may be reversed, if needed, without having to re-orient the laser source through the opposite laser port.

Also shown in dashed line format is the extension of the bolt 77 through the open bore 83 and threaded bore 87 which act to hold the first manifold section 35 and second manifold section 37 together. Also shown in dashed line format is one of the bolts 67 extending into base portion 47. In this manner, the flow cell assembly 9 which was shown in FIG. 1 is joined into a sturdy assembly.

Referring to FIG. 5, a section taken along line 5—5 of FIG. 2 illustrates further details of the encapsulation support 151. First laser port 191 is shown is in communication with a threaded aperture 231 which leads into accommodation space 153. An opposing threaded aperture 233, which is in alignment with threaded aperture 231 leads into a second laser port 235. In the section of FIG. 5, the light transmission bores 158, 163 and 165 are also seen.

In assembling the test stand of the present invention, the first and second manifolds 35 and 37 and the flow cell assembly 9 are oriented with their upper planar portions 45 and 49, respectively oriented downwardly and their base portions 47 and 51, respectively, oriented upwardly. The flow bore 25 of the flow cell 11 is aligned with the small bores 221 and 225 which are the flow bores in their respective manifolds, since much of the structures occupying optical apertures 121 and 223 do not admit flow. Next, the pair of o-rings 31 and 33 are sandwiched on either side of the flow cell 11, each surrounding an opening of the flow bore 25 of the flow cell. Next the first and the second manifolds 35 and 37 are compressibly joined together to compress the o-rings 31 and 33 against the flow cell 11 and against the first and second manifolds 35 and 37. This is performed with the bolts 75 and 77 engaged through the open bores 81 and 83 and into the threaded bores 85 and 87. Next, the base plate 61 is attached to the base portions 47 and 51 of the compressibly joined first and second manifolds 35 and 37 to form flow cell assembly 9.

The assembled test stand, which is not shown in assembled form, but which is shown going into such assembled form in FIG. 2 is accomplished by placing the flow cell assembly 9 into accommodation space 153 an encapsulation support 151, in a fit which will align the laser ports 191 and 235 into optical communication with the flow bore 25 of the flow cell 11. The flow cell assembly 9 may be attachably joined into the accommodation space 153 of the encapsulation support 151 using bolts (not shown) threaded through the apertures 154, 155, 156 and 157 and into the threaded apertures 171, 173, 175, and 177.

For light scattering instruments which incorporate many detection angles in the read head, the use of vertical pins, such as pins 99 and 101, used to horizontally align the flow cell assembly 9 is an encumbrance because the pins 99 and 101 tend to block some of the detection angles.

Figure 6:
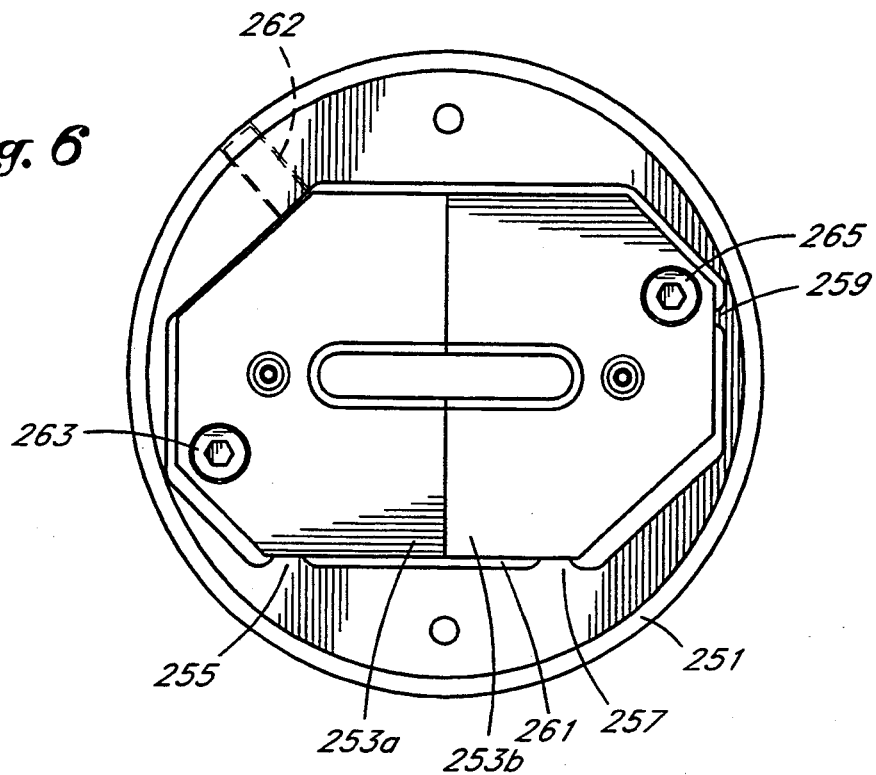
FIG. 6 is a view from above an alternate assembled flow cell assembly and its encapsulation support.

An alternate way of ensuring accurate horizontal alignment of a flow cell assembly in a encapsulation support is shown in FIG. 6. A round read head 251 is used to support a flow cell assembly 253, having halves 253a and 253b. Within the encapsulation support 251, a series of three pads 255, 257, and 259 on two vertical surfaces of an accomodation space 261. The three pads 255, 257, and 259 serve as alignment stops for the flow cell assembly 253. The flow cell assembly 253 is pushed against the stops by a spring plunger 262 which also allows the flow cell assembly 253 to be removed and re-inserted into the read head 251.

The flow cell assembly 253 is secured to the read head by two bolts 263 and 265, and is vertically aligned by four bosses, similar to the bosses 105 107 111 and 113 in a manner entirely similar to the configuration of FIGS. 1-5.

Figure 7:
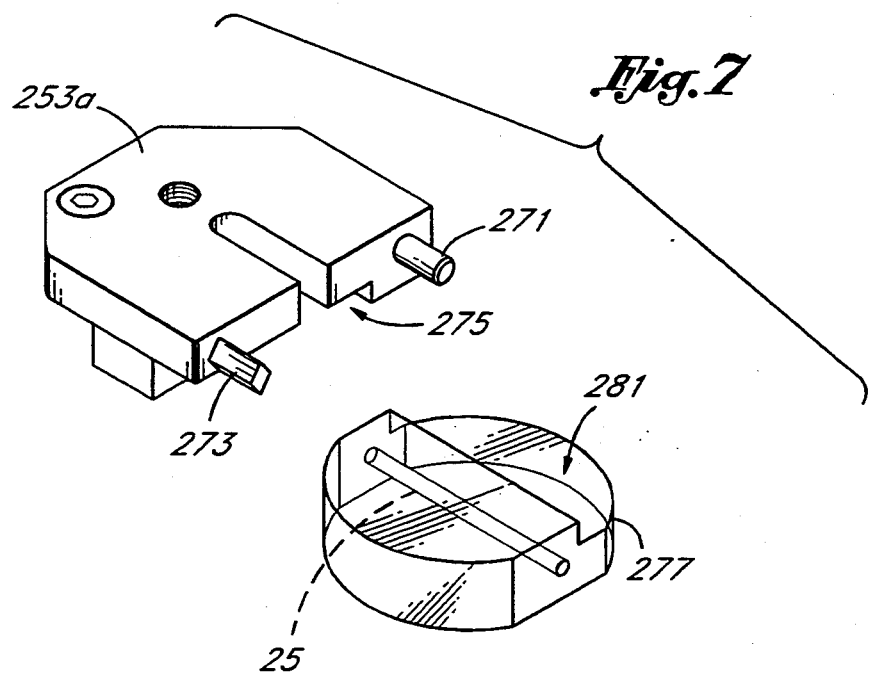
FIG. 7 is an exploded view of part of the flow cell assembly of FIG. 6.

The configuration shown in FIGS. 1 and 2 is self aligning in the vertical direction, but will require manual alignment of the flow cell 11 in the horizontal plane. A method for creating self alignment is illustrated in FIG. 7. A one half section 253a of the upper portion of the flow cell assembly 253 shown in FIG. 6 is illustrated as having alignment pins 271 and 273. The lower surface of the section 253a has a step 275 which extends across the surface of the half section 253a. A flow cell 277 is shown, similar to flow cell 11, and having a step 281 extending across its surface. The step 281 is complementary to the step 275 and provides horizontal alignment.

The step 281 extends axially along the top of the cell 277 parallel to the flow bore 25. Both of the halves 253a and 253b carry the step 275 in the bottom of their planar sections. When mated, the two steps 281 and 275 will ensure that the flow bore 25 will be aligned with the two manifold section 253a and 253b bores. During assembly, the operator should maintain a horizontal force on the flow cell 253 in order to maintain contact between the steps 281 and 275 and the manifold sections 253a and 253b and the cell 277.

While the present invention has been described in terms of a laser flow cell, one skilled in the art will realize that the structure and techniques of the present invention can be applied to a structure which may be utilized in many appliances. The present invention may be applied in any situation where flow and optical propagation is desired and where precision, stability, and repeatability is needed. Further, the flow cell of the present invention may be applied in any situation where the facilitation of ease of assembly and cleaning is needed in such a rigid and stable structure.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A flow cell assembly comprising:
   a first manifold section having an upper planar portion having a face end and a second end and a base portion defining a first optical opening;
   a second manifold section having an upper planar portion having a face end and a second end and a base portion defining a second optical opening;
   means for attaching said first manifold section to said second manifold section joining said face ends;
   a base plate attachable to said base portions of said first and said second manifold sections;
   a flow cell mountable between said base portions and between said upper planar portions and said base plate, and in conjunction with said first and second manifold sections establishing a fluid flow path from an opening defined by said first manifold section, through said flow cell, through and to an opening defined by said second manifold section, said first optical opening in communication with said second optical opening through a portion of said fluid flow path;
   means for attaching said base plate to said base portion of said first and second manifold sections
   optical sealing means, secured to said first and said second optical openings, for sealing said optical openings and facilitating the propagation of light through said optical openings.

2. The flow cell assembly recited in claim 1 wherein said first manifold section defines a pair of open bores extending longitudinally through said upper planar portion from said face end to said second end, and wherein said second manifold section defines a pair of threaded bores extending longitudinally into said face of said upper planar portion, and wherein said means for attaching said first manifold section to said second manifold section joining said face ends further comprises a pair of bolts extending through said open bores and threadably engaging said pair of threaded bores to secure said face end of said upper planar portion of said first manifold section to said face end of said upper planar portion of said second manifold section.

3. The flow cell assembly recited in claim 1 wherein said base portion of said first and second manifold sections each defines at least one threaded bore and wherein said base plate defines a plurality of apertures, with at least one of said plurality of apertures aligned with at least one said threaded bore of each of said base portions and wherein said means for attaching said base plate to said base portion of said first and second manifold sections are bolts threadably engagable with at least one said threaded bore of each of said base portions.

4. The flow cell assembly recited in claim 1 wherein said flow cell further comprises a glass structure having an upper planar surface parallel to a lower planar surface, a first flat end surface at one end of said flow cell adjacent to both upper and lower planar surfaces, a second flat end surface at the other end of said flow cell and adjacent to both upper and lower planar surfaces and parallel to said first flat end surface, and a first curved surface bridging said first and second flat end surfaces and adjacent so both said upper and lower planar surfaces, and a second curved surface bridging said first and second flat end surfaces and adjacent to both said upper and lower planar surfaces, and opposite said first curved surface, said flow cell defining a flow bore extending from said first flat end surface to said second flat end surface.

5. The flow cell assembly recited in claim 4 wherein said flow bore opens onto said first and said second flat end surfaces at their geometric center.

6. The flow cell assembly recited in claim 1 wherein said first and said second optical openings have an interior surface and wherein said optical sealing means further comprises:
   an o-ring seal sealingly engaging said interior surface of said optical opening;
   an optical window abutting said o-ring seal; and
   an optical window retainer abutting said optical window.

7. The flow cell assembly recited in claim 1 wherein said face end of said first manifold section carries a plurality of alignment pins and wherein said face end of said second manifold section carries a plurality of apertures, each one of said alignment pins fittable within an associated one of said apertures of said face end of said second manifold section.

8. The flow cell assembly recited in claim 1 wherein said base plate has a circular center section and a pair of rectangular ends, said circular center section approximately the same size as an abutting surface of said flow cell, and each of said pair of rectangular ends of approximately the same size as an abutting surface of said base portion.

9. A flow cell assembly comprising:
   a first manifold section having an upper planar portion having a face end and a second end and a base portion and defining an optical opening and defining a pair of open bores extending longitudinally through said upper planar portion from said face end to said second end;
   a second manifold section having an upper planar portion having a face end and a second end and a base portion and defining an optical opening defining a pair of threaded bores extending longitudinally into said face of said upper planar portion;
   a pair of bolts extending through said open bores and threadably engaging said pair of threaded bores to secure said face end of said upper planar portion of said first manifold section to said face end of said upper planar portion of said second manifold section;

a base plate attachable to said base portions of said first and said second manifold sections;

a flow cell mountable between said base portions and between said upper planar portions and said base plate, and defining a flow bore in optical alignment with said first and second optical openings of said base portions.

10. A supported flow cell assembly, including the flow cell assembly of claim 9 and wherein said upper planar portions of said first and said second manifold sections define a first plurality of apertures, and further comprising:

an encapsulation support having an accommodation space for interfitting with and supporting said flow cell assembly, said encapsulation support having a second plurality of threaded apertures opening into said accommodation space and each of which align with an associated one of said first plurality of apertures of said upper planar portions of said first and said second manifold sections; and a plurality of bolts extendable through said first plurality of apertures of said upper planar portions of said first and said second manifold sections and threadably engaged with said second plurality of threaded apertures in said encapsulation support.

11. The flow cell assembly recited in claim 9 wherein said upper planar portions of said first and said second manifold sections form a multi sided planar structure.

12. A supported flow cell assembly, including the flow cell assembly of claim 11 and wherein said upper planar portions of said first and said second manifold sections define a plurality of apertures, and further comprising:

an encapsulation support having an accommodation space having vertical walls which extend generally parallel to the sides of said multi sided planar structure for interfitting with and supporting said flow cell assembly, said encapsulation support having a plurality of threaded apertures opening into said accommodation space and each of which align with an associated one of said apertures of said upper planar portions of said first and said second manifold sections, and having at least two contact pads along vertical walls for aligning said flow cell assembly;

a spring contact extending from at least one wall of said encapsulation support for urging said flow cell assembly against said contact pads; and a plurality of bolts extendable through said apertures of said upper planar portions of said first and said second manifold sections and threadably engaged with said plurality of threaded apertures.

13. The flow cell assembly recited in claim 9 wherein said first and second manifold sections have underside surfaces defining an alignment structure, and wherein said flow cell has an upper surface having an alignment structure matable with said alignment structure of said first and second manifold sections.

14. A process of assembling a flow cell into a flow cell assembly comprising the steps of:

orienting the first and second manifolds with their upper planar portions oriented downwardly and their base portions oriented upwardly;

aligning the flow bore of a flow cell with a flow bore in said first manifold and with a flow bore in said second manifold;

sandwiching a pair of o-rings on either side of said flow cell, each surrounding an opening of said flow bore of said flow cell;

compressibly joining said first and said second manifolds together to compress said o-rings against said flow cell and against said first and second manifolds; and attaching a base plate to said base portions of said compressibly assembled said first and second manifolds to form a flow cell assembly.

15. The process of assembling a flow cell test stand, including the steps of assembling a flow cell assembly as recited in claim 14 and further comprising the steps of:

placing said flow cell assembly into an accommodation space of an encapsulation support having laser ports in optical communication with said flow bore of said flow cell; and attachably joining said flow cell assembly into said accommodation space of said encapsulation support.

16. A flow cell assembly for a liquid stream to be analyzed using a beam of light, the flow cell assembly comprising:

a transparent flow cell including opposed end facets and an axial bore extending through the flow cell between the end facets, first and second manifold sections, each section including a facet to mate against a facet of the transparent flow cell and a bore collinear with the bore of a mated flow cell, the first section being positioned at one end of the flow cell and the second section being positioned at the other, opposed end of the flow cell, first alignment means to establish and hold the manifold sections together and in alignment such that their bores are collinear; and second alignment means to establish and hold the flow cell against the manifolds and in alignment such that the flow cell bore is collinear with the manifold bores.

17. A flow cell assembly as set forth in claim 16 including means to seal the flow cell facets to the manifold section facets.

18. A flow cell assembly as set forth in claim 16 in which the flow cell has a cylindrically axial bore extending along a diameter of the flow cell and perpendicular to the opposed end facets.

19. A flow cell assembly as set forth in claim 16 in which the first alignment means includes mating pins and sockets in the manifold sections that engage one another.

20. A flow cell assembly as set forth in claim 19 in which the manifold sections abut one another when the flow cell assembly is held together by the alignment means, one of the manifold sections including projecting pins, the other of the manifold sections including sockets receiving the projecting pins.

21. A flow cell assembly as set forth in claim 16 and further comprising an encapsulation support having an accommodation space for interfitting with and supporting said flow cell assembly in which the first alignment means includes one or more pins protruding from the lower planar surfaces which mate with corresponding holes in the top surface of the accommodation space of the encapsulation support.

22. A flow cell assembly as set forth in claim 16 and further comprising an encapsulation support having an accommodation space for interfitting with and supporting said flow cell assembly in which the first alignment means includes two or more vertical surfaces in the accommodation space of the encapsulation support serving as pads which guide corresponding vertical surfaces of the planar sections of the cell assembly manifolds.

23. A flow cell assembly as set forth in claim 16 in which the second alignment means includes a step in a horizontal surface of the flow cell parallel to the bore which mates with a corresponding step in a horizontal surface of at least one of the manifolds.

24. A flow cell for use in a flow cell assembly to contain a liquid stream to be analyzed using a beam of light, the flow cell comprising:
- a transparent substantially cylindrical body,
- an bore through a diameter of the substantially cylindrical body,
- a planar end facet at each end of the body, the bore extending between and terminating at the planar end facets, and
- a window in the side of the body through which liquid flowing in the bore may be viewed.

25. A flow cell for use in a flow cell assembly as set forth in claim 24 wherein said transparent substantially cylindrical body further comprises flat, parallel upper and lower faces.

26. A flow cell for use in a flow cell assembly as set forth in claim 25 wherein said transparent substantially cylindrical body further comprises a circular, cylindrical window.

27. A flow cell for use in a flow cell assembly as set forth in claim 26 including a pair of windows, each located a short distance away from said end facets.

* * * * *